(12) United States Patent
Eschbach

(10) Patent No.: US 11,389,071 B2
(45) Date of Patent: Jul. 19, 2022

(54) SURGICAL DEVICE INCLUDING SYSTEM FOR SENSING TISSUE PROPERTIES AND METHODS THEREOF

(71) Applicant: Covidien LP, Mansfield, MA (US)

(72) Inventor: Matthew Eschbach, Cheshire, CT (US)

(73) Assignee: COVIDIEN LP, Mansfield, MA (US)

( * ) Notice: Subject to any disclaimer, the term of this patent is extended or adjusted under 35 U.S.C. 154(b) by 706 days.

(21) Appl. No.: 16/262,161

(22) Filed: Jan. 30, 2019

(65) Prior Publication Data

US 2019/0320918 A1 Oct. 24, 2019

Related U.S. Application Data

(60) Provisional application No. 62/661,821, filed on Apr. 24, 2018.

(51) Int. Cl.
*A61B 5/0215* (2006.01)
*A61B 5/021* (2006.01)
*A61B 5/00* (2006.01)

(52) U.S. Cl.
CPC ...... *A61B 5/02154* (2013.01); *A61B 5/02141* (2013.01); *A61B 5/6885* (2013.01); *A61B 5/7239* (2013.01)

(58) Field of Classification Search
CPC ............ A61B 5/02154; A61B 5/02141; A61B 5/6885; A61B 5/7239
See application file for complete search history.

(56) References Cited

U.S. PATENT DOCUMENTS

| 2008/0255433 | A1* | 10/2008 | Prough | A61B 5/7239 600/301 |
| 2009/0062667 | A1* | 3/2009 | Fayram | A61B 5/349 600/486 |
| 2010/0185220 | A1 | 7/2010 | Naghavi et al. | |
| 2013/0023776 | A1* | 1/2013 | Olde | A61M 1/3656 600/487 |
| 2014/0249573 | A1 | 9/2014 | Arav | |
| 2015/0032012 | A1* | 1/2015 | Marinello | A61B 5/0022 600/486 |

(Continued)

OTHER PUBLICATIONS

Extended European Search Report dated Sep. 24, 2019 corresponding to counterpart Patent Application EP 19170614.2.

(Continued)

*Primary Examiner* — Catherine B Kuhlman
*Assistant Examiner* — Sean A Frith
(74) *Attorney, Agent, or Firm* — Carter, DeLuca & Farrell LLP

(57) ABSTRACT

The present disclosure relates to systems and methods of detecting a tissue property during a laparoscopic surgical procedure with a tissue property sensing device. The method may include positioning a sensing assembly disposed along a distal portion of a tissue property sensing device about target tissue in a body cavity, inflating a bladder to compress and occlude blood flow of the target tissue, sensing a pressure measurement of pressure in the bladder and a light amplitude measurement of light projected through the target tissue, and determining a systolic blood pressure of the target tissue based on the pressure measurement and the light amplitude measurement.

21 Claims, 10 Drawing Sheets

(56) References Cited

U.S. PATENT DOCUMENTS

| | | | |
|---|---|---|---|
| 2015/0157326 A1* | 6/2015 | Schiemanck | A61B 5/6853 |
| | | | 606/194 |
| 2016/0183819 A1* | 6/2016 | Burnett | A61B 5/14507 |
| | | | 600/309 |
| 2016/0199092 A1 | 7/2016 | Patel et al. | |
| 2016/0256076 A1* | 9/2016 | Kassab | A61B 5/1076 |
| 2017/0146390 A1* | 5/2017 | Kovacs | A61B 5/02055 |
| 2017/0251927 A1* | 9/2017 | Takoh | A61B 5/6824 |
| 2017/0360313 A1* | 12/2017 | Baek | A61B 5/02108 |
| 2018/0192900 A1* | 7/2018 | Wei | A61B 5/02141 |
| 2018/0296744 A1* | 10/2018 | Solem | A61M 1/3656 |
| 2019/0175216 A1 | 6/2019 | Williams | |

OTHER PUBLICATIONS

U.S. Appl. No. 62/597,621 (now U.S. Appl. No. 16/140,664), filed Dec. 12, 2017, entitled Surgical Instruments Including System for Sensing Tissue Properties and Methods Thereof.

\* cited by examiner

SURGICAL DEVICE INCLUDING SYSTEM FOR SENSING TISSUE PROPERTIES AND METHODS THEREOF

CROSS-REFERENCE TO RELATED APPLICATION

This application claims the benefit of and priority to U.S. Provisional Patent Application No. 62/661,821 filed Apr. 24, 2018, the entire disclosure of which is incorporated by reference herein.

BACKGROUND

Technical Field

The present disclosure relates generally to surgical devices and, more particularly, to systems and methods for measuring one or more tissue properties during a surgical procedure.

Related Art

During surgical procedures medical professionals or clinicians may find it desirable to determine one or more tissue properties prior to acting upon the tissue. For example, during colorectal surgeries which require anastomosis, the clinician visually inspects the tissue of the colon to be resected. Typically, during inspection, the clinician visually observes the colon and determines which portion or portions of the colon are diseased. The clinician then identifies which diseased portions of the colon will be removed. Observation may be performed via one or more imaging devices positioned within the colon or proximate to the colon. Various other surgical procedures require similar visual inspection of tissue to determine which portions of tissue are to be removed.

Depending on the procedure and the tissue being examined, the clinician may not identify all areas of concern due to the limited visibility of the clinician. For example, referring again to anastomotic procedures, the colon may include an abnormal growth which may not be easily visualized from an inspection of the exterior of the colon. As such, the clinician may need to inspect the interior of the tissue to be resected as well. Inspection of the interior of the colon may require additional clinicians to assist in imaging the interior of the colon. Additionally, care must be taken when aligning the interior and exterior views during the imaging process.

As such, improved systems and methods for evaluating tissue properties during a surgical procedure are desirable.

SUMMARY

Existing challenges associated with the foregoing, as well as other challenges, are overcome by methods for identifying one or more properties of target tissue, and also by systems, and apparatuses that operate in accordance with the methods.

In accordance with an aspect of the present disclosure, a surgical device for sensing a tissue property includes a handle, an outer cannula, an actuation assembly slidably received by the outer cannula, and a sensing assembly. The handle is coupled to the outer cannula. The actuation assembly is slidably received by the outer cannula. The sensing assembly includes a fixed member, a shuttle, a sensor, and a bladder. The fixed member is disposed along a distal portion of the outer cannula. The shuttle is configured to slidably engage the fixed member. The sensor is disposed on the shuttle. The bladder is configured to be in fluid communication with bladder pressurization devices.

In aspects, the surgical device further includes a fluid conduit coupled to the bladder. The fluid conduit may be configured to be coupled to a bladder pressurization device. The actuation assembly may include an inner cannula. The inner cannula may be configured to be slidably received by the outer cannula. The handle, the outer cannula, and the inner cannula may include corresponding openings configured to permit passage of a fluid conduit therethrough.

According to aspects, the shuttle may further include an arm including at least one tooth disposed along the arm of the shuttle. The fixed member may further include an arm including at least one tooth configured to selectively engage the at least one tooth of the arm of the shuttle. The bladder may be configured to selectively engage the arm of the fixed member. The arm of the fixed member may be biased toward the center of the outer cannula.

In aspects, the surgical device may include a first spring disposed along a proximal portion of an inner cannula. The first spring may be configured to apply a proximal force to a knob coupled to a proximal portion of the inner cannula. The first spring may be configured to apply a distal force to a pin coupled to the handle. The surgical device may include a second spring disposed between the fixed member and the shuttle. The second spring may be configured to engage the sensing assembly. The second spring may be configured to apply a distal force to the fixed member. The second spring may be configured to apply a proximal force to the shuttle.

According to aspects, the first spring and the second spring may be configured to maintain the surgical device in a closed position. The actuation assembly may be configured to receive a distal force sufficient to overcome the force applied by the first spring and the second spring to cause the actuation assembly to engage the sensing assembly. The actuation assembly may be configured to apply force to the target tissue when the sensing assembly is positioned about the target tissue while the proximal force is applied by the first spring or the second spring to cause the sensing assembly to move proximally toward the closed position.

In aspects, when the bladder of the surgical device is expanded, the bladder may be configured to apply a force to the target tissue to cause the target tissue to engage the sensor. The bladder may be configured to apply sufficient force to occlude blood flow through the target tissue. The sensor may be selected from the group consisting of piezoresistive force sensors, optical sensors, and impedance sensors.

According to an aspect of the present disclosure, a method of detecting a tissue property during a laparoscopic surgical procedure with a tissue property sensing device is disclosed. The method includes positioning a sensing assembly disposed along a distal portion of a tissue property sensing device about target tissue in a body cavity, inflating a bladder to compress and occlude blood flow of the target tissue, sensing a pressure measurement of pressure in the bladder and a light amplitude measurement of light projected through the target tissue, and determining a systolic blood pressure of the target tissue based on the pressure measurement and the light amplitude measurement.

In aspects, sensing may include sensing a plurality of pressure measurements and a corresponding plurality of light amplitude measurements taken at a plurality of times as pressure in the bladder is reduced. Pressure in the bladder may be determined to be less than or equal to a lower operational threshold. Sensing may include waiting to sense the plurality of pressure measurements and the plurality of light amplitude measurements until the pressure in the bladder is less than or equal to an upper operational threshold.

According to aspects, a root mean square (RMS) of the plurality of light amplitude measurements may be determined, and a subset of light amplitude measurements corresponding to a pulse based on the RMS may be identified. The identified light amplitude measurements corresponding to the pulse may have a greater value than the RMS multiplied by a signal-to-noise ratio (SNR). A systolic blood pressure may be determined based on the pressure measurements associated with a first pulse exceeding a predetermined threshold and/or a calculated threshold. A diastolic blood pressure may be determined based on the pressure measurements associated with a last pulse falling below a predetermined threshold and/or a calculated threshold.

According to aspects, the RMS may be multiplied by the SNR to determine a noise threshold, and the light amplitude measurements whose value is less than the noise threshold may be discarded when identifying a subset of light amplitude measurements corresponding to the pulse. A systolic blood pressure may be determined based on the pressure measurements associated with the pulse. A plurality of pulses may be identified. A pulse rate may be determined based on the identified plurality of pulses.

In aspects, a systolic blood pressure may be determined based on the pressure measurements associated with the plurality of pulses. A diastolic blood pressure may be determined based on the pressure measurements associated with the plurality of pulses.

According to aspects, a systolic blood pressure may be determined based on the pressure measurements associated with a first pulse. A diastolic blood pressure may be determined based on the pressure measurements associated with a last pulse.

A systolic blood pressure may be identified based on the sensing. The sensing may include sensing a first pressure measurement and a first light amplitude measurement taken at a first time, and a second pressure measurement and a second light amplitude measurement taken at a second time, the first light amplitude measurement being less than the second light amplitude measurement.

According to aspects, a start point and a stop point of depressurization may be identified based on the plurality of pressure measurements.

In aspects, at least one pulse may be identified based on the plurality of light amplitude measurements. A plurality of pulses may be identified based on the plurality of light amplitude measurements.

According to aspects, a systolic blood pressure may be identified based on the plurality of pulse measurements. The systolic pressure may be the pressure measured at a first pulse from among the plurality of pulses.

In aspects, a peak light amplitude measurement may be identified based on the plurality of light amplitude measurements. A beginning of each pulse may be identified. The beginning of each pulse may occur at the time where a light amplitude measurement is both greater than a previous light amplitude measurement and a light amplitude threshold. The light amplitude threshold may be calculated as the value of the peak light amplitude measurement multiplied by a predetermined value. A systolic blood pressure may be identified based on the pressure measurements associated with a first pulse. A diastolic blood pressure may be identified based on the pressure measurements associated with a last pulse. A root mean square (RMS) may be calculated based on the plurality of light amplitude measurements. A noise threshold may be determined based on the RMS.

According to aspects, determining the noise threshold may include setting the noise threshold as the RMS multiplied by a signal-to-noise ratio (SNR). The light amplitude measurements which are less than the noise threshold may be determined to be noise signals not associated with a pulse. An error signal may be transmitted when no pulse is detected. A signal may be transmitted to display the systolic blood pressure.

BRIEF DESCRIPTION OF THE DRAWINGS

The accompanying drawings, which are incorporated in and constitute a part of the specification, illustrate embodiments of the present tissue sensing devices and methods and, together with a general description of the disclosure given above, and the detailed description of the embodiment(s) given below, serve to explain the principles of the disclosure.

DETAILED DESCRIPTION

Figure 1:
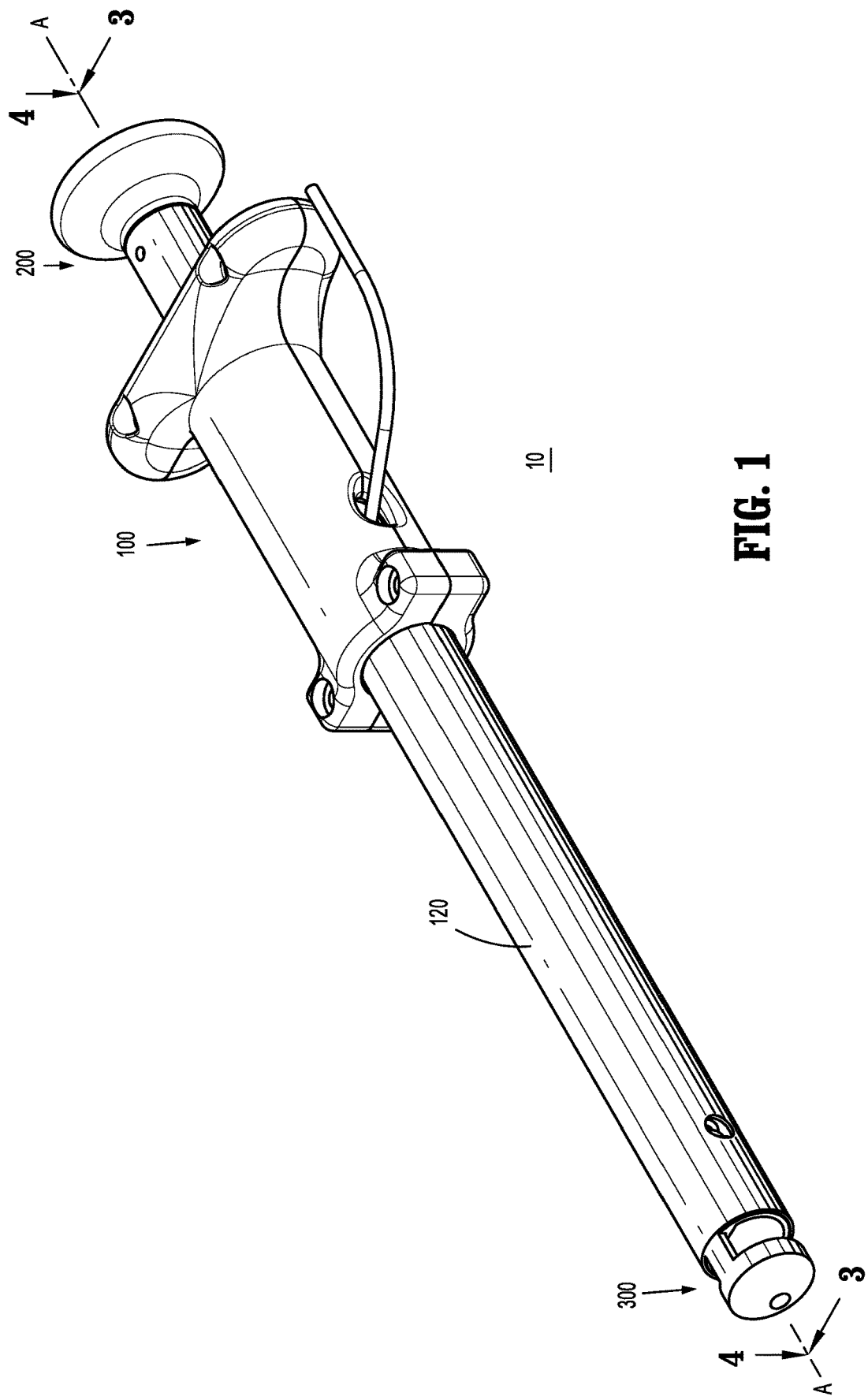
FIG. 1 is a perspective view of a tissue property sensing device in accordance with an embodiment of the present disclosure.

Embodiments of the present tissue sensing instruments or devices and methods are described in detail with reference to the drawings, in which like reference numerals designate identical or corresponding elements in each of the several views.

Reference will be made to the terms described herein while describing the principles outlined by the present disclosure. As used herein, the term "clinician" refers to a doctor, nurse, or other care provider and may include support personnel. The term "distal" refers to structure that is, in use, positioned farther from the clinician, while the term "proximal" refers to structure that is closer to the clinician. Further, directional terms such as front, rear, upper, lower, top, bottom, distal, proximal, and the like are used to assist in understanding the description and are not intended to limit the present disclosure. The term "surgical field" refers to the space in which the surgical procedure is performed, and the term "surgical cavity" refers to a cavity at least partially surrounded by tissue.

Tissue property sensing devices in accordance with illustrative embodiments of the present disclosure include a handle coupled to an outer cannula, an actuation assembly, and a sensing assembly. In use, the clinician applies distal force to a knob of the tissue property sensing device to advance a shuttle of the sensing assembly distally relative to a distal portion of the tissue property sensing device. After the shuttle is advanced distally relative to the outer cannula the tissue property sensing device is in an "OPEN" configuration, and the target tissue is positioned with a cavity formed by the shuttle. Once the clinician is satisfied with the placement of the target tissue within the cavity, the clinician releases the distal force applied to the knob while maintaining a grasp on the tissue property sensing device. As force applied to the knob is applied or reduced, the tissue property sensing device and, more particularly, the sensing assembly is maintained in fixed relation to the target tissue while the target tissue is pinned or clamped between components of the sensing assembly. When the target tissue is clamped, one or more properties are measured by sensors associated with the sensing assembly. The sensing assembly may be further coupled to a bladder pressurization device (not shown). To increase the force applied to the target tissue, the bladder pressurization device may be engaged, thereby causing gas or fluid (referred to herein as "fluid" for clarity) to be selectively maintained in the bladder.

Referring initially to FIG. 1, one embodiment of a tissue property sensing device is shown and generally referred to as a surgical device 10. The surgical device 10 defines a longitudinal axis A-A and includes a handle 100, an actuation assembly 200, and a sensing assembly 300. The handle 100 includes an outer cannula 120 extending through a bore defined by the handle 100, wherein the bore extends along the longitudinal axis A-A. The outer cannula 120 is configured to slidably receive the actuation assembly 200 therein, the actuation assembly 200 moving proximally and distally relative to the outer cannula 120.

With reference to FIGS. 1-4, the actuation assembly 200 is configured to move proximally and distally along the longitudinal axis A-A relative to the outer cannula 120. The actuation assembly 200 includes an inner cannula 220 which is slidably received along an interior surface defined by the outer cannula 120. The inner cannula 220 defines a proximal portion 220a and a distal portion 220b. The proximal portion 220a of the inner cannula 220 is configured to couple to a knob 202. The knob 202 includes a proximal engagement surface 204 which is indented distally to facilitate engagement of the knob 202 by the thumb of a clinician. Similarly, the outer surface of the knob 202 has a frustoconical shape configured to receive proximal forces exerted by clinicians during surgical procedures. The knob 202 may receive proximal or distal forces, and in response to receiving the respective force, cause the inner cannula 220 to move relative to the outer cannula 120 between a proximal-most position (FIG. 5C) and distal-most position (FIG. 5A). Movement of the inner cannula 212 between proximal and distal positions causes the inner cannula 212 to selectively engage the sensing assembly 300.

The sensing assembly 300 is configured to, when engaged by the inner cannula 220, apply or reduce force exerted on target tissue (not shown) when the target tissue is located along an interior portion of the sensing assembly 300. As force is applied or relieved from the sensing assembly 300, the target tissue may be compressed or decompressed, thereby facilitating selective engagement of the tissue with a sensor assembly "S" (FIG. 3) associated with the sensing assembly 300. In embodiments, the sensors assembly "S" includes a first sensor "S1" disposed on the proximal-facing surface of the compression head 302a, and a sensor light emission device or light "S2" disposed on the balloon "B". Both the first sensor "S1" and the second sensor "S2" may be placed in opposing positions (e.g., the first sensor "S1" may be located where the second sensor "S2" is positioned, and vice versa) or adjacent positions. The first sensor "S1" may be a photodetector configured to receive signals from the light "S2" upon transmission of light from the second sensor "S2". The light "S2" may be any suitable light emitting device, such as a light-emitting diode (LED), and the like. In use, the light "S2" is configured to transmit and/or reflect light to the first sensor "S1". More particularly, the light "S2" is configured to transmit light at one or more predetermined frequencies which, when received by the first sensor "S2" after passing through tissue is converted into sensor data associated with one or more tissue properties, described later in greater detail. In embodiments the first sensor "S1" and the light "S2" may be positioned on any of the components of the sensing assembly 300 so as to transmit and receive light through tissue which is positioned within the sensing assembly 300. Additionally, or alternatively, fluid may be introduced to the surgical device 10, such as gases or liquids, which cause a bladder "B" (see FIGS. 2-5C) of the surgical device 10 to engage the target tissue.

Figure 3:
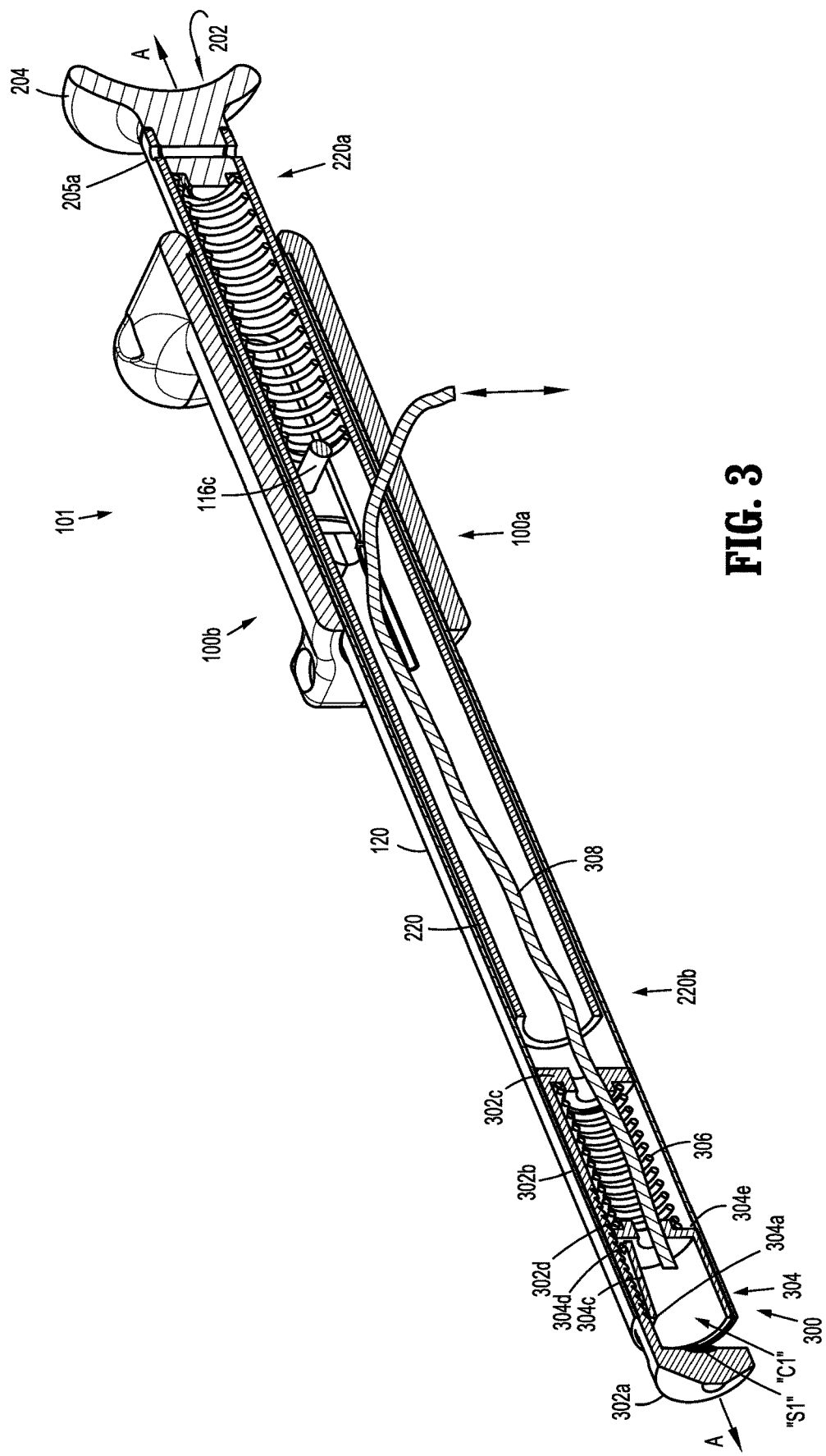
FIG. 3 is a perspective view of the tissue property sensing device of FIG. 1, taken along section line 3-3 of FIG. 1.

In embodiments, the first sensor "S1" may include both a transmitter configured to transmit light and a sensor or receiver configured to receive the transmitted light. More particularly, the transmitter may transmit light which is reflected by target tissue. The reflected light may subsequently be received or sensed by the receiver which, upon reception, transmits reflected light measurements or sensor measurements to a controller "C" (FIG. 3).

Figure 2:
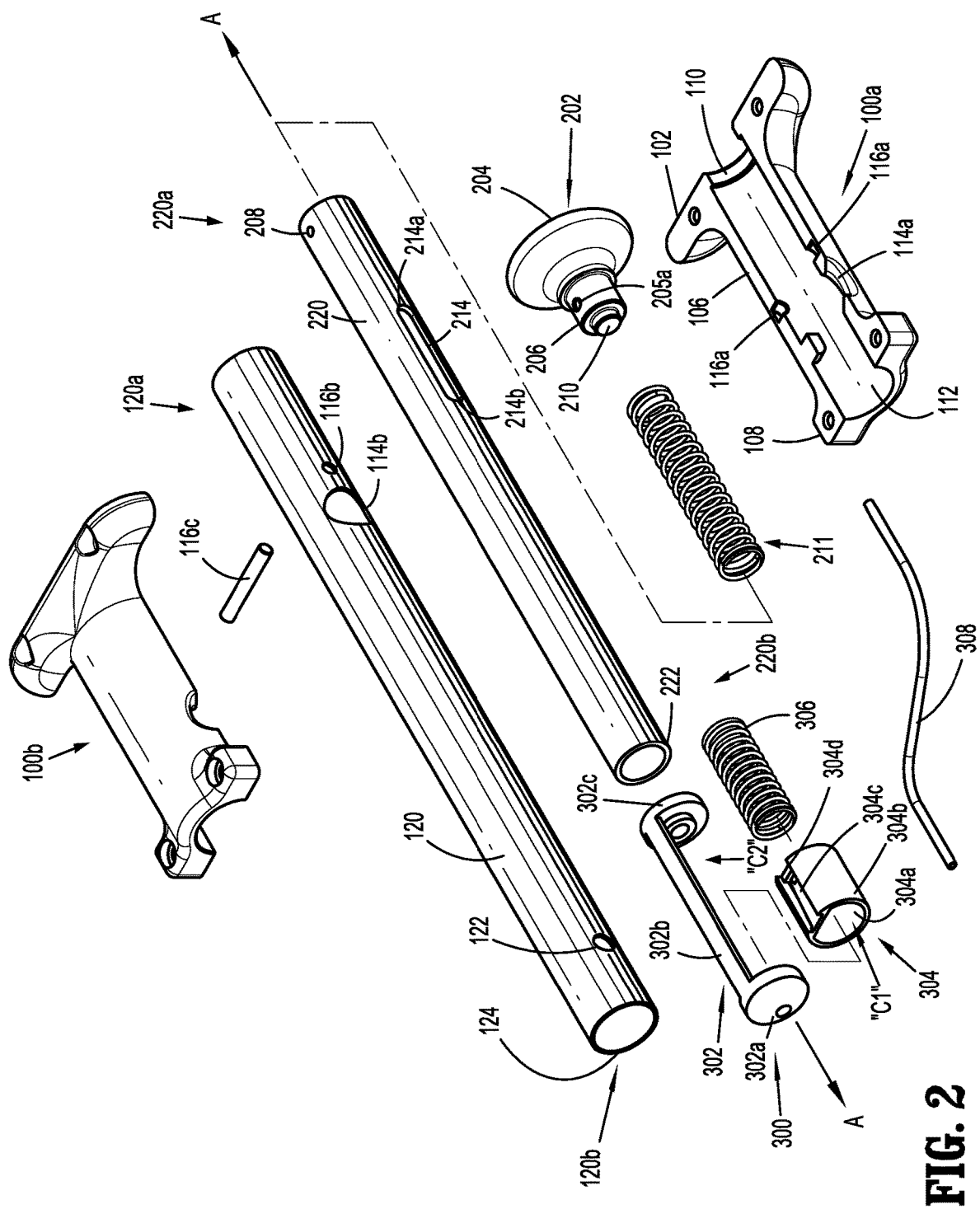
FIG. 2 is an exploded perspective view of the tissue property sensing device of FIG. 1.

Referring to FIG. 2, as illustrated by the disassembled surgical device 10 of FIG. 1, the handle 100 includes a first half portion 100a and a second half portion 100b. The first and second half portions 100a, 100b are in mirrored relation and are configured to be coupled to and about a proximal portion of the outer cannula 120. For purposes of clarity the handle 100 will be described when the first half portion 100a and second half portion 100b are coupled. The handle 100 includes a proximal flange 102 and a distal flange 108. The proximal flange 102 is located proximal to a body portion 106 of the handle 100. The distal flange 108 is located distal to the body portion 106. The body portion 106 is configured to be gripped by the hand of a clinician (not shown), with the proximal flange 102 and the distal flange 108 further configured to receive force exerted by the clinician and provide support as the clinician grasps the surgical device 10.

The handle 100 is configured to couple about a proximal portion of the outer cannula 120. When the handle 100 is coupled about the outer cannula 120, an inner surface 112 of the handle 100 is positioned adjacent to the proximal portion of an outer surface defined by the outer cannula 120. Corresponding fastening openings or bores 104 disposed in fixed relation along the handle 100 may receive fasteners therein (not shown) when the handle 100 is coupled to the proximal portion of the outer cannula 120, thereby fixably coupling the handle 100 to the outer cannula 120.

The handle 100 includes a pair of opposing lateral recesses 116a which are configured to receive a pin 116c therein. The pin 116c is additionally received by openings 116b of the outer cannula 120 therethrough. As a result, when the surgical device 10 is engaged by a clinician, the handle 100 remains in a fixed position relative to the outer cannula 120.

The handle 100 further includes an opening 114a which align with an opening 114b of the outer cannula 120. The openings 114a, 114b permits passage of a fluid conduit 308 through the handle 100 and the outer cannula 120, respectively.

The outer cannula 120 is configured to slidably receive an inner cannula 220 of the actuation assembly 200 therein. The inner cannula 220 includes a base connection opening 208, a pair of windows 214, and a distal engagement portion 222. The knob 202 includes a distal member 206 configured to be inserted into a proximal portion 220a of the inner cannula 220. The distal member 206 includes an opening 205a defining a bore extending transverse relative to axis A-A. When the knob 202 is inserted into the proximal portion 220a of the inner cannula 220, and the opening 205a is aligned with the base connecting opening 208, a pin (not shown) may be inserted therethrough to maintain the knob 202 in fixed relation to the inner cannula 220.

The windows 214 extend longitudinally parallel to the A-A axis, and are configured to receive one or more fluid conduits 308 therethrough. The windows 214 includes a proximal portion 214a and a distal portion 214b configured to limit motion of the inner cannula 220 relative to the outer cannula 120. More particularly, as the inner cannula 220 is translated proximally or distally relative to the outer cannula 120 the pin 116c, extending through the windows 214, engages the proximal portion 214a or the distal portion 214b of the windows 214. As a result, when the pin 116c engages the proximal portion 214a or the distal portion 214b of the windows 214, the inner cannula 212 reaches a limit and is prevented from translating further in the direction which the inner cannula 212 was traveling. It should be noted that the windows 214 may not be in mirrored relation so as to prevent engagement or crimping of fluid conduits 308 extending through the window 214 by the outer cannula 120 or inner cannula 220.

The handle 100 further includes a spring 211 positioned between a nub 210 extending distally from the knob 202 and the pin 116c. When positioned between the knob 202 and the pin 116, the spring 211 is configured to transmit proximal and distal forces against both the nub 210 and the pin 116c, respectively. As the spring 211 transmits proximal and distal forces to the nub 210 and the pin 116c, the transmitted force causes the knob 202 to be biased to a proximal position relative to the surgical device 10 by default. When a distal force is applied to the knob 202, the knob 202 is translated distally relative to the spring 211. In response to the application of distal force to the knob 202, the spring 211 is configured to compress, permitting slidable translation of the inner cannula 220 along a portion of the outer cannula 120.

The windows 214 may be configured to limit motion of the inner cannula 220 relative to the outer cannula 120. More particularly, as the inner cannula 220 translates relative to the outer cannula 120, the proximal portion 214a and the distal portion 214b of the window 214 may be positioned along the inner cannula 220 such that the proximal and distal portions 214a, 214b of the window 214 contact the pin 116c once the inner cannula 220 is translated to a proximal-most or distal-most position. Depending on the placement of the windows along the inner cannula, one window 214 may prevent the crimping or obstruction of the flow of fluid through the fluid conduit 308 by limiting translation of the window 214 which receives the fluid conduit 308 therethrough. Additionally, the windows 214 are configured to limit rotation of the inner cannula 220 relative to the outer cannula 120.

Figure 4:
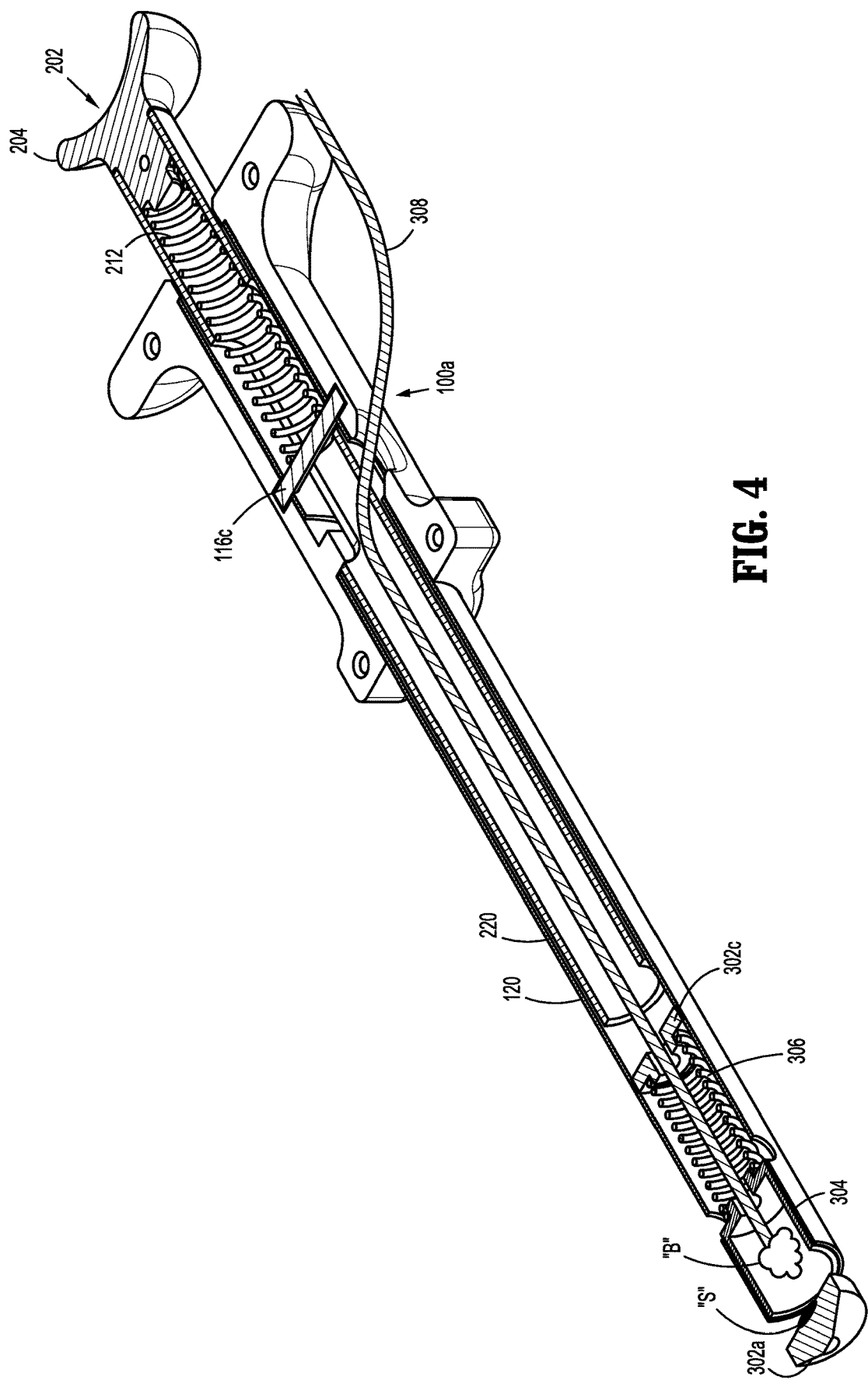
FIG. 4 is a perspective view of the tissue property sensing device of FIG. 1, taken along section line 4-4.
Figure 5A:
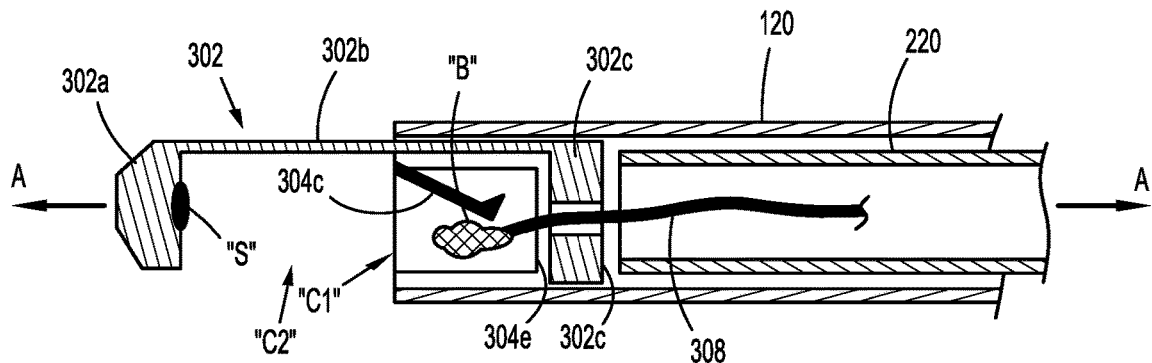
FIG. 5A is a side plan view of the tissue property sensing device of FIG. 1 in an open configuration, taken along 3-3.
Figure 5B:
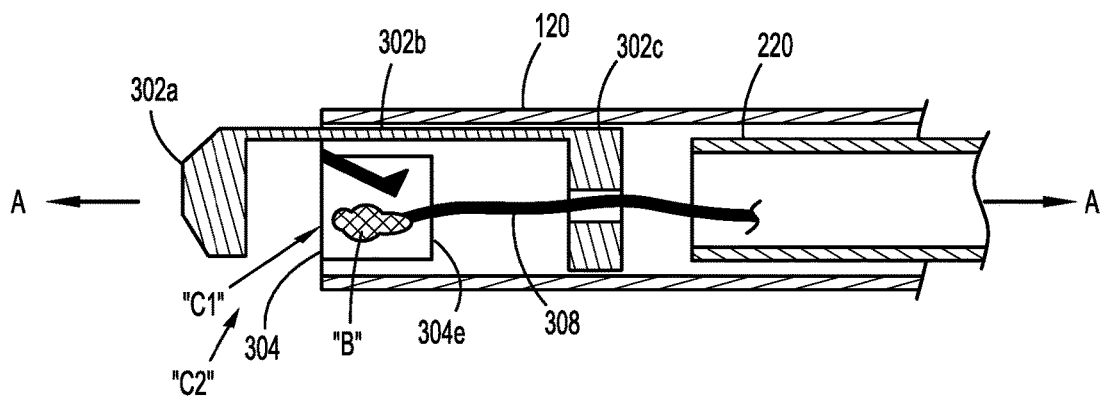
FIG. 5B is a side plan view of the tissue property sensing device of FIG. 1 in a closed configuration, with a bladder deflated, taken along 3-3.
Figure 5C:
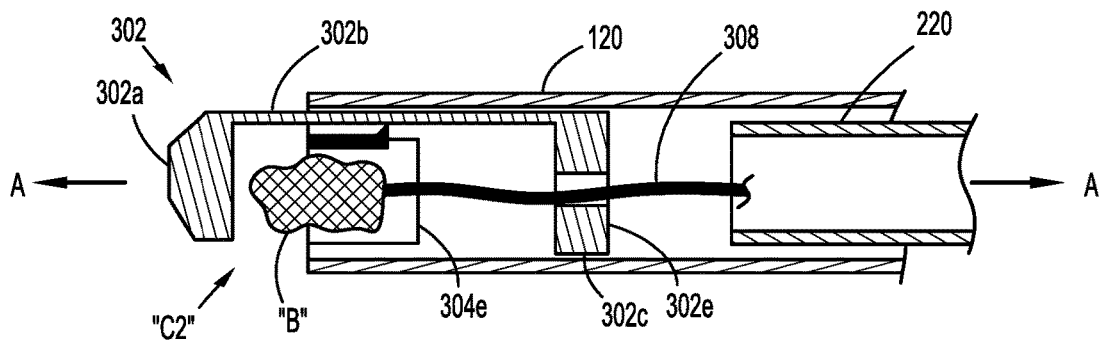
FIG. 5C is a side plan view of the tissue property sensing device of FIG. 1 in a closed configuration, with the bladder inflated, taken along 3-3.

Referring now to FIGS. 1-4, and specifically FIGS. 3 and 4, the sensing assembly 300 is shown coupled to a distal portion of the outer cannula 120. The sensing assembly 300 is configured to be engaged by the inner cannula 220 and by a bladder pressurization device (not shown). The sensing assembly 300 includes a fixed member 304 coupled (fixed) internally along the proximal portion 120a of the outer cannula 120. The fixed member 304 includes an outward-biased arm or biasing arm 304c and a spring receiving member 304e. The fixed member 304 further defines a recess or opening "C1" located within the distal portion 120a of the outer cannula 120. The inner surface 304a, defined by the fixed member 304, is configured to slidably receive a shuttle arm 302b of a shuttle 302 therethrough. The biasing arm 304c further defines one or more teeth 304d configured to engage teeth 302d disposed along the shuttle arm 302b. Absent the application of radial force from the bladder "B", the biasing arm 304c is configured to be biased toward the central portion of the fixed member 304.

The sensing assembly 300 further includes a shuttle 302 having a shuttle head or compression head 302a, the shuttle arm 302b, and a shuttle base 302c. The compression head 302a and shuttle base 302c are coupled proximally and distally to the shuttle arm 302b, respectively. The shuttle arm 302b further defines a set of teeth which are configured to be engaged by the one or more teeth of the shuttle arm 302b. The compression head 320a includes a sensor assembly "S" disposed on an inner proximally facing surface of the compression head 320.

The sensing assembly 300 further includes a spring 306 is positioned between the fixed member 304 and the shuttle base 302c. The spring 306 is configured to apply proximal and distal forces to the shuttle base 302c and the spring receiving member 304e, respectively. As a result, absent engagement of the sensing assembly 300 by the inner cannula 220 or the bladder pressurization device (not shown), the sensing assembly 300 is configured to remain in a "CLOSED" position by default. The sensing assembly 300 is maintained in the "CLOSED" position by the spring 306 which exerts proximal and distal forces to the shuttle base 302c and the spring receiving member 304e. To transition the sensing assembly 300 from the "CLOSED" position (FIG. 5C) toward the "OPEN" position (FIG. 5A), force is applied to the shuttle 302 by the distal engagement portion 222 of the inner cannula 220. When sufficient force is exerted on the knob 202 by clinicians to overcome force exerted on the shuttle 302 by the spring 306, the shuttle 302 advances distally relative to the outer cannula 120, thereby transitioning the sensing assembly 300 to the "OPEN" position.

The sensing assembly 300 also includes a bladder "B" positioned in a cavity "C1" defined by the fixed member 304. The bladder "B" is coupled to the fluid conduit 308. As noted earlier, the fluid conduit 308 is in fluid communication with a compressor or bladder pressurization device (not shown), and operably couples the bladder "B" to the bladder pressurization device. The bladder "B", when in a distended or expanded state, is configured to apply force outward toward an inner surface 304a defined by the fixed member 304, and the compression head 302a. Alternatively, when in a deflated state, the bladder "B" is configured to reduce or eliminate the outward force applied during expansion of the bladder "B". More particularly, when target tissue is positioned between the bladder "B" and the compression head 302a, as the bladder "B" is expanded, outward force is directed toward the compression head 302a and received at least in part by the target tissue positioned therebetween. It is contemplated that the bladder "B" may be attached to the fixed member 304 via an adhesive, a hook and loop fastener, a suture, or the like. It is further contemplated that the bladder "B" may be detachably coupled to the fixed member 304.

When the bladder "B" is expanded, the bladder "B" also applies force, radially outward, toward the biasing arm 304c of the fixed member 304. Once sufficient outward force is applied by the bladder "B" to the biasing arm 304c, the teeth 302d of the shuttle arm 302b engage the teeth 304d of the biasing arm 304c. Engagement of the shuttle arm 302b by the teeth 304d of the biasing arm 304c limits distal motion of the shuttle 302, thereby preventing the shuttle 302 from advancing distally when toward the distal-most or "OPEN" position.

As noted earlier, the proximal surface of the compression head 302a of the shuttle 302 includes at least one first sensor "S1" disposed thereon. The first sensor "S1" may include one or more sensors which may be fixed to the proximal surface of the compression head 302a via any suitable method including, but not limited to, fixation with an adhesive, one or more fasteners (not shown), clips or other similar structures disposed along the compression head 302a. The sensor first "S1" may include one or more piezoresistive force sensors, optical sensors, photodetectors, or impedance sensors.

The first sensor "S1" and/or the light "S2" may be in wired or in wireless communication with a computing device 400 (FIG. 6) such as a controller "C" (FIG. 3) which is coupled or otherwise in electrical communication with a display device (not shown). In embodiments the controller "C" may be disposed within or about the tissue property sensing device 10. It is contemplated that, in embodiments, the controller "C" may be located remotely, either in wired or wireless electrical communication with the first sensor "S1" and the light "S2". The first sensor "S1" is configured to transmit sensor signals therefrom and, more particularly, as the first sensor "S1" is engaged by the tissue during a sensing procedure, the first sensor "S1" is configured to transmit sensor signals to the controller "C" indicative of blood profusion, tissue health, blood force, blood profusion, tissue impedance, tissue profusion, etc.

The handle 100, outer cannula 120, inner cannula 220, actuation assembly 200 and sensing assembly 300 may be manufactured using materials known in the art, such as plastics, polymers, biocompatible materials, metals, and other similar materials known in the art. The fluid conduit 308 may be made of plastics, rubbers, or other similar materials capable of delivering pressurized fluids to the bladder "B". The bladder may be fabricated from a biocompatible material such as natural or synthetic elastomers, natural or synthetic rubbers, silicone materials, and/or compliant elastomers.

For a detailed description of the mechanical operation of a tissue property sensing device 10, reference may be made to U.S. Provisional Patent Application No. 62/597,621, filed on Dec. 12, 2017, entitled "SURGICAL INSTRUMENTS INCLUDING SYSTEM FOR SENSING TISSUE PROPERTIES AND METHODS THEREOF," the entire contents of which are hereby incorporated by reference in their entirety.

Reference will now be made to operation of the surgical device 10 during a surgical procedure performed by a clinician. When the clinician determines that it would be desirable to measure one or more tissue properties during a surgical procedure, the clinician may insert the distal portion of the surgical device 10 into a surgical cavity of a patient. The surgical device 10, and more particularly the sensing assembly 300, may be in the "CLOSED" position due to force applied by the springs 211, 306 so as to prevent inadvertent engagement of tissue by the sensing assembly 300. The bladder "B" may additionally be distended while the surgical device 10 is guided toward the target tissue to prevent inadvertent distal motion of the shuttle 302 relative to the surgical device 10. Once inserted, the clinician may guide the distal portion of the surgical device 10 toward target tissue.

After identifying the target tissue, while the bladder "B" is deflated, the clinician may grasp the handle 100 and apply distal force to the knob 202 relative to the handle 100. As distal force is applied to the knob 202, the clinician applies an approximately equal amount of counter force to the handle 100, so as to maintain the handle 100 in fixed relation to the tissue. While distal force is applied to the knob 202, the distal portion 220b of the inner cannula 220 applies force distally to the shuttle base 302c. In turn, the shuttle base 302c transfers the distal force to both the shuttle arm 302b and the compression head 302a, thereby causing the compression head 302a to advance distally toward an "OPEN" position. Concomitantly, the spring 306 is compressed between the distal portion 220b of the inner cannula 220 and the shuttle base 302c of the shuttle 302.

Once in the "OPEN" position, the sensing assembly 300 may be positioned around the target tissue by positioning the target tissue within a cavity "C2" of the shuttle 302. More particularly, the target tissue is positioned between the compression head 302a and the distal portion 120b of the outer cannula 120. Once the target tissue is situated such that the majority of the target tissue is positioned central to the longitudinal axis A-A, the clinician may reduce or release the distal force exerted on the knob 202. In response, the shuttle 302, and more specifically the compression head 302a, is advanced proximally toward the fixed member 304 and engages the target tissue, e.g., clamps the target tissue.

The bladder "B" may be partially or fully expanded prior to release of distal force by the clinician on the knob 202. As the target tissue is compressed between the compression head 302a and the bladder "B", or the distal portion 120b of the outer cannula 120, the target tissue is fixed in position relative to the surgical device 10. The clinician may then engage the bladder pressurization device, thereby causing fluid force to build up in the bladder "B". The increase in fluid force in the bladder "B" causes the target tissue to be further compressed between the bladder "B" and the compression head 302a. Additionally, the increase in force fixes the compression head 302a relative to the outer cannula 120 as the bladder "B" presses the biasing arm 304c into engagement with the teeth 304d of the shuttle arm 304b. In embodiments, a computing device 400 (FIG. 6) may transmit control signals to cause the bladder pressurization device to inflate or deflate the bladder "B". More particularly, the bladder pressurization device may receive signals to inflate or deflate Once the desired amount of compression is exerted on the target tissue, the first sensor "S1" may transmit sensor signals to the computing device 400 (FIG. 6) to be displayed on a display (not shown). The sensor signals may be generated by projecting light from the light "S2" to the first sensor "S1", the light also projected through target tissue disposed between the first sensor "S1" and the light "S2". In embodiments, the light "S2" may be disabled depending on the tissue property being sensed. It is contemplated that, in embodiments, the light "S2" may be substituted for another sensor similar to the first sensor "S1". The display (not explicitly shown) may display data indicative of the sensor measurements at a specified time, at periodic intervals, or continuously. Once the desired sensor measurements are noted by the clinician, the clinician may cause the bladder pressurization device to reduce the force applied by the bladder "B". In embodiments, the controller "C" may control operation of the tissue property sensing device 10, including compression and decompression of the bladder "B" as well as collection of sensor signals from the first sensor "S1" and transmission of light from the light "S2". As force is released, bladder "B" permits the teeth 304d located on the biasing arm 304c of the fixed member 304 to disengage the teeth 302e of the shuttle arm 302b, which in turn permits the clinician to apply distal force to the knob 202 to free the target tissue from the surgical device 10. As the clinician applies distal force, the compression head 302a extends distally. Once the target tissue is free from the surgical device 10, the clinician may cease applying distal force to the knob 202, and allow the surgical device 10, and more particularly the sensing assembly 300, to return to the "CLOSED" position.

Figure 6:
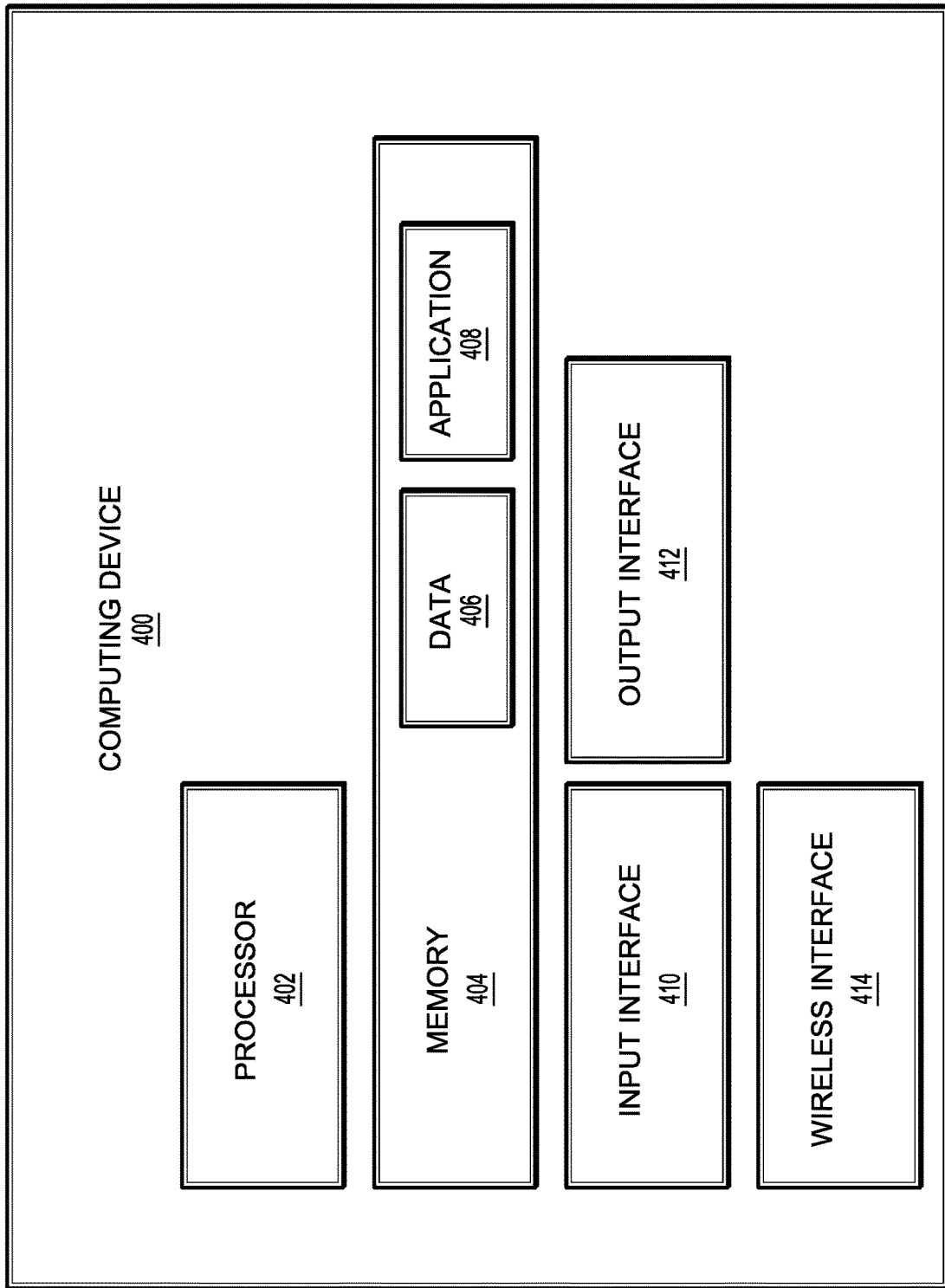
FIG. 6 is a schematic block diagram of a computing device that may be employed according to various embodiments of this disclosure.

Referring now to FIG. 6, illustrated is a schematic block diagram of a computing device 400 that may be employed according to various embodiments of the present disclosure. Though not explicitly shown in corresponding figures of the present application, the computing device 400, or one or more components thereof, may represent one or more components (e.g., a controller, input interface, output interface, and the like) of the surgical device 10. The computing device 400 may include one or more processors 402, memories 404, input interfaces 410, output interfaces 412, wireless interfaces 414, or any desired subset of components thereof. The memory 404 includes non-transitory computer-readable storage media for storing data and/or software which include instructions that may be executed by the one or more processors 402. When executed, the instructions may cause the processor 402 to control operation of the computing device 400, e.g., reception and transmission of sensor signals transmitted and received during operation of the first sensor "S1" and the light "S2" located along the surgical device 10 (FIG. 3). More particularly, the computing device 400 may receive the sensor signals, indicative of one or more light amplitude measurements, and store the sensor signals in the memory 404 of the computing device 400. The sensor signals indicative of the light amplitude measurements may be stored with supplemental information including, but not limited to, time stamp information associated with the reception of the signals, device information associated with the device receiving the sensor signals, and the like. In embodiments, the memory 404 includes non-transitory computer-readable storage media for storing data and/or software which includes instructions that may be executed by the one or more processors 402. The memory 404 may include one or more solid-state storage devices such as flash memory chips. Additionally, or alternatively, the memory 404 may include one or more mass storage devices in communication with the processor 402 through a mass storage controller and a communications bus (not shown). Although the description of computer readable media described in this disclosure refers to a solid-state storage device, it will be appreciated by one of ordinary skill that computer-readable media may include any available media that can be accessed by a processor 402. More particularly, computer readable storage media may include, without limitation, non-transitory, volatile, non-volatile, removable, non-removable media, and the like, implemented in any method of technology for storage of information such as computer readable instructions, data structures, program modules, or other suitable data access and management systems. Examples of computer-readable storage media include RAM, ROM, EPROM, EEPROM, flash memory, or other known solid state memory technology, CD-ROM, DVD, Blu-Ray, or other such optical storage, magnetic cassettes, magnetic tape, magnetic disk storage or other magnetic storage devices, or any other medium which may be used to store information and which can be accessed by computing device 400.

In embodiments, the memory 404 stores data 406 and/or one or more applications 408. Such applications 408 may include instructions which are executed on the one or more processors 402 of the computing device 400. The applications 408 may include instructions which cause an input interface 410 and/or an output interface 412 to receive and transmit sensor signals, respectively, to and from the surgical device 10. More particularly, as the at least one sensor "S" (see FIG. 3) senses one or more of the tissue properties discussed above, the at least one sensor "S" may, in response, transmit signals indicative of the measurements to the input interface 410, or by an external computing device 400. Once received by the input interface 410, the signals transmitted by the one or more sensors "S" may be stored in the at least one memory 404 of the computing device 400. Additionally, or alternatively, the computing device 400 may transmit the signals for analysis and/or display via the output interface 412. For example, the output interface 412 may transmit the sensor signals to a display device (not shown) either disposed on the surgical device 10 or located remotely relative to the surgical device 10. The memory 404 may further transmit and/or receive data via a wireless interface 414 via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)). Although depicted as a separate component, the wireless interface 414 may be integrated into the input interface 410 and/or the output interface 412.

Figure 7A:
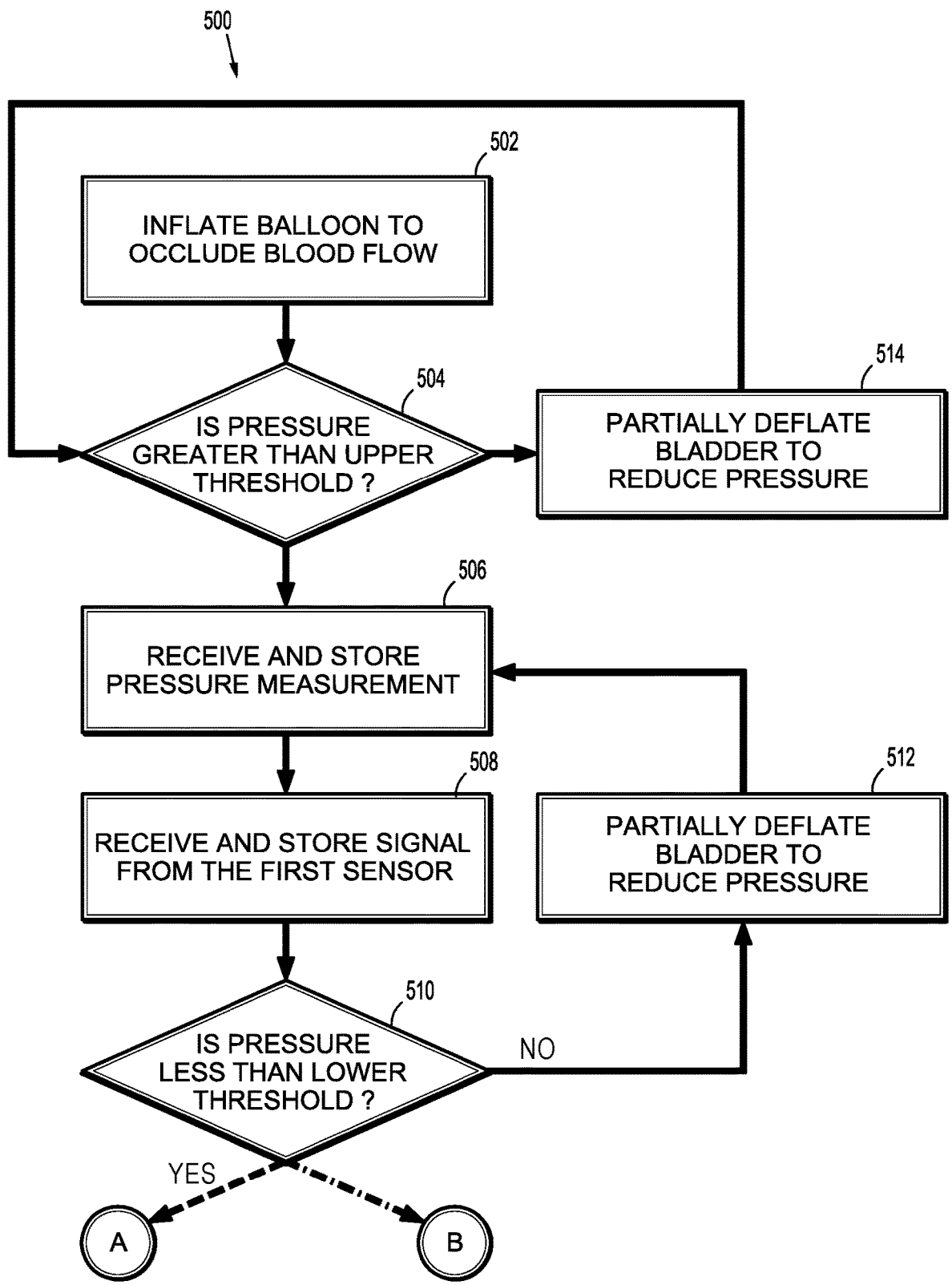
FIGS. 7A-7C illustrate a flow diagram showing an illustrative method for measuring a tissue property of target tissue when the target tissue is being manipulated.
Figure 7B:
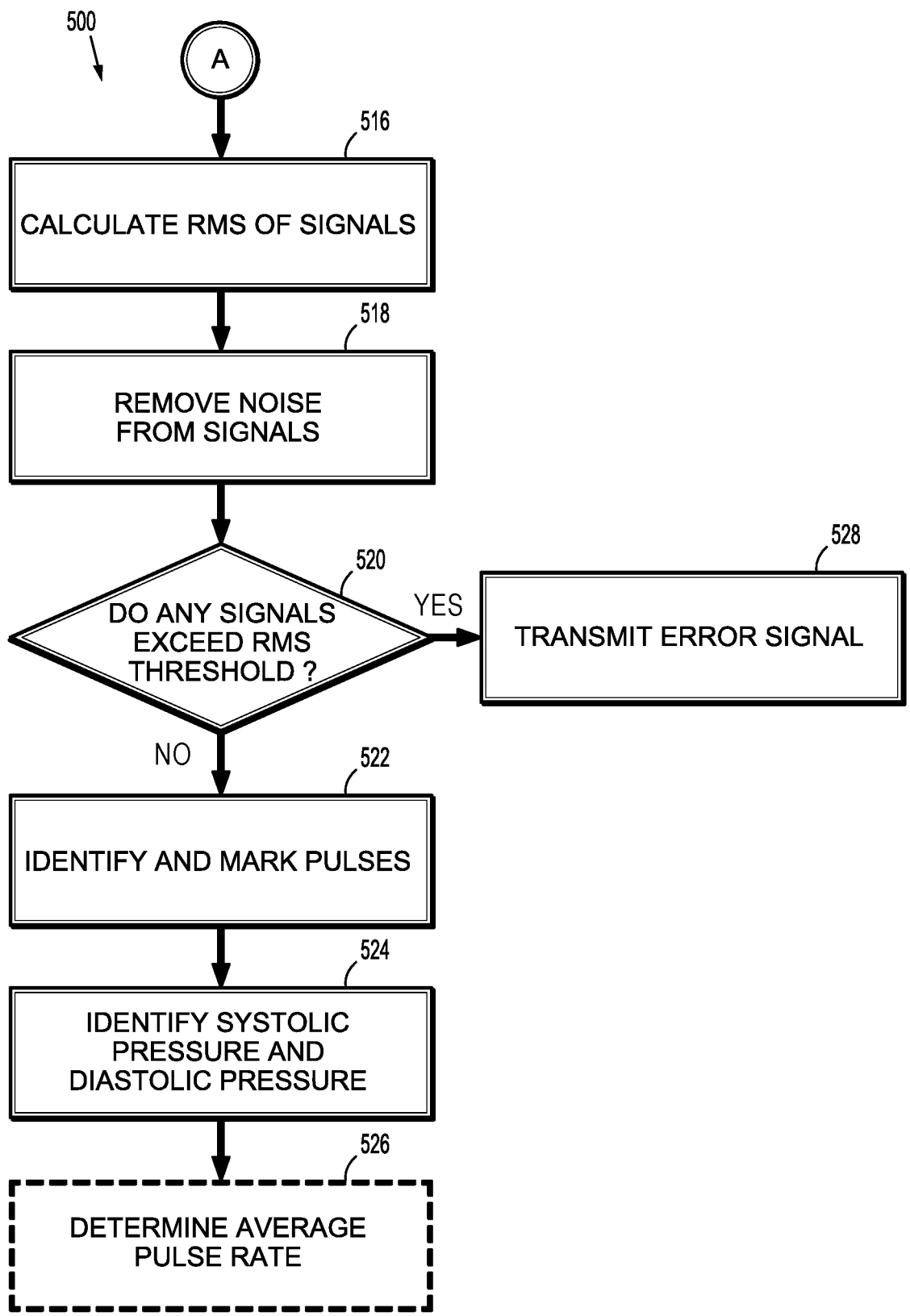
Figure 7C:
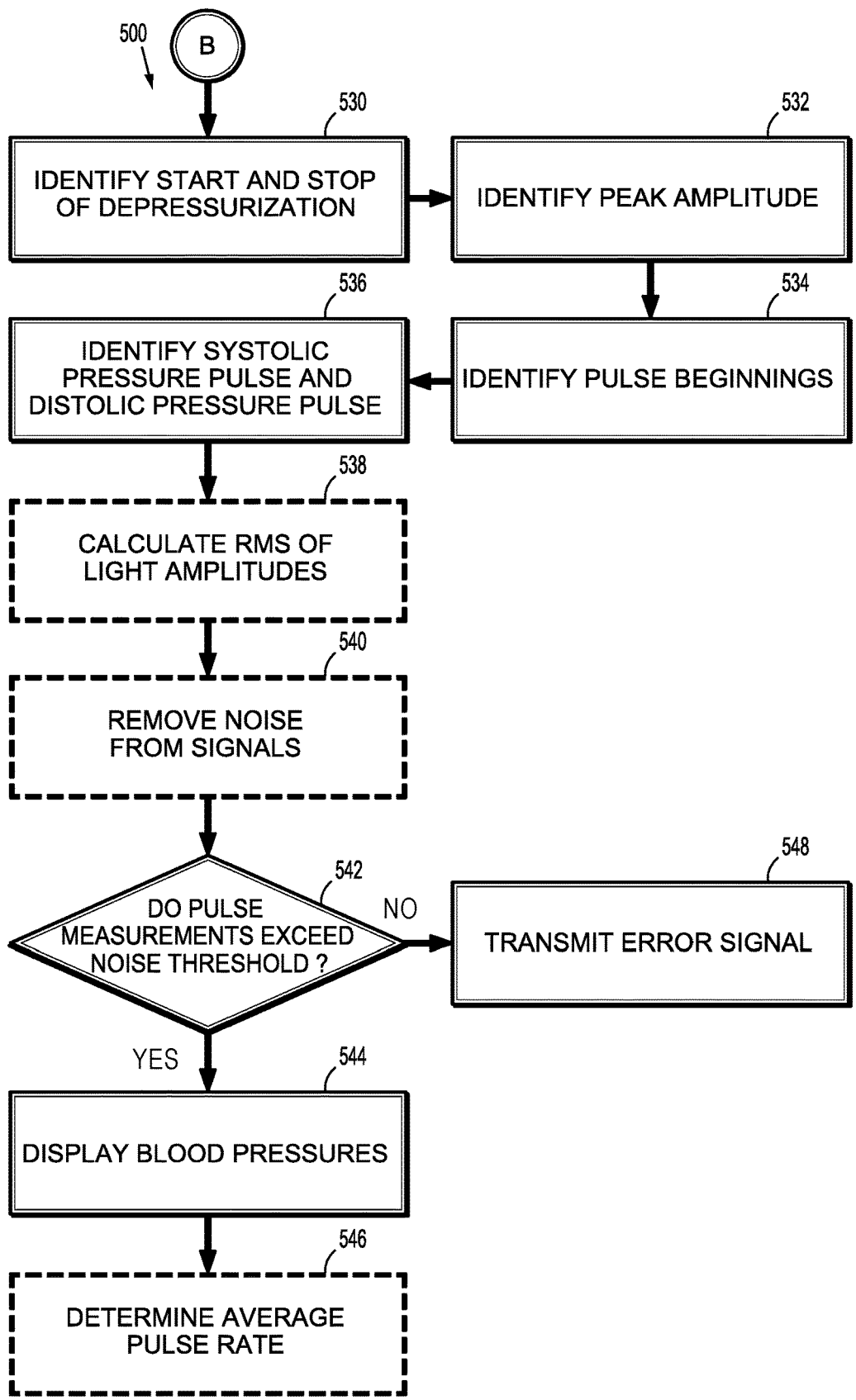

Referring now to FIG. 7, illustrated is a method for measuring a tissue property of target tissue when the target tissue is being manipulated, the method designated generally process 500.

Initially, at block 502, the controller "C" (FIG. 3), which is similar in many respects to the computing device 400 (FIG. 6), controls the tissue property sensing device 10, and causes the bladder pressurization device (e.g., an air compressor) to transmit fluid (e.g., air) to the bladder "B". In embodiments, it is contemplated that any suitable devices may be used to pressurize the bladder including, without limitation, fluid compressors, pumps, syringes, manual bulbs, and the like. Such contemplated devices may be controlled manually by clinicians or, alternatively, may be controlled by the computing device 400. This fluid transmission in turn causes the bladder "B" to inflate or otherwise expand, compressing target tissue disposed between the bladder "B" and the proximal-facing surface of the compression head 302a. As pressure is exerted on the target tissue, a pressure sensor (not explicitly shown) coupled to, and in fluid communication with, the bladder pressurization device measures the pressure of the fluid entering the bladder "B". It is contemplated that, in embodiments, the pressure sensor may be disposed along a portion of the fluid conduit 308, within or about the bladder "B", or along any other component in fluid communication with the bladder "B". The measured pressure is then transmitted to the controller "C" as a sensor signal.

At block 504, the computing device 400 determines, based on the pressure measured in the bladder "B", whether the measured pressure is greater than an operational pressure range having both an upper operational threshold and a lower operational threshold between which the tissue property sensing device 10 may accurately operate to measure systolic and/or diastolic pressures. If the pressure measured in the bladder "B" is greater than the upper operational threshold, process 500 continues to block 514 and the pressure in the balloon "B" is reduced. This measurement and reduction of pressure in the bladder "B" at blocks 504 and 514, respectively, is repeated until the sensed pressure in the bladder "B" is equal to or less an upper operational pressure. Once the pressure in the balloon "B" is equal to or less than the upper operational pressure, process 500 begins to monitor the target tissue engaged by the tissue property sensing device 10.

At block 506 the controller "C" of the tissue property sensing device 10 receives sensor signals (e.g., pressure signals) from the pressure sensor and stores the signals as pressure measurements indicating the pressure in the balloon "B" at a particular time during the sensing procedure. Additionally, at block 508 the controller "C", in response to sending a signal to the light "S2" to begin transmitting light toward the first sensor "S1", receives signals from the first sensor "S1" associated with the amplitude of the light (hereinafter "light amplitude measurements") received by the first sensor "S1". Both the pressure measurements and the light amplitude measurements received by the controller "C" are stored and associated with their respective time when they were measured in the memory 204 of the controller "C". In embodiments, the time may be measured from the point at which the pressure of the bladder "B" is determined to be equal to or less than the upper operational threshold.

At block 510, the computing device 400 determines whether the pressure measurement measured at block 506 is less than the lower operational threshold (e.g., the lowest pressure at which the tissue property sensing device 10 may operate). If the controller "C" determines that the pressure of the bladder "B" is greater than or equal to the lower operational threshold, process 500 continues to block 512, and the controller "C" sends a signal to cause the bladder pressurization device to decrease the pressure in the bladder "B". Process 500 may continuously measure and store both the pressure measurements and the light amplitude measurements at blocks 506 and 508, respectively. As the controller "C" receives the pressure and light amplitude measurements, the controller "C" stores the measurements in the memory 204 of the controller "C". The measurements may be stored in an array, or any such suitable data structure, so as to provide a chronological index of the measurements taken during operation of the tissue property sensing device 10 between the upper and lower pressure thresholds of the operational pressure range, as well as the time at which the pressure measurements were taken. For purposes of clarity, the analysis of these measurements by the computing device will be discussed with respect to time measurements taken over a period T, from time t=0 to time t=n, where t=0 represents the time at which the pressure and light amplitude begin to be recorded, and time t=n represents the time at which the pressure in the bladder "B" is less than the predetermined threshold at which the tissue property sensing device 10 can no longer sense either the pressure or the light amplitude with the desired accuracy.

Once the controller "C" determines that the pressure in the bladder "B" is less than the lower pressure threshold, the tissue property sensing device 10 may stop taking and storing pressure and light amplitude measurements. In embodiments, the tissue property sensing device 10 may release the target tissue (e.g., may deflate the bladder "B" and/or transition the tissue property sensing device 10 to the OPEN configuration), or alternatively, may apply or maintain pressure to the target tissue to maintain the position of the target tissue relative to the tissue property sensing device 10, prior to release of the target tissue.

When identifying blood pressure (either systolic and/or diastolic blood pressure) based on the light amplitude measurements sensed by the tissue property sensing device 10, the controller "C" may either analyze the collected signals with a band-pass filter (method A) or, additionally or alternatively, after transforming the light amplitude signals (method B), to isolate pulses of blood flow through the target tissue. In embodiments, the controller "C" may perform either operation, or both, either independently or concurrently, to identify the systolic and diastolic blood pressures.

With reference to the band-pass method (method A), at block 516, the controller "C" may, in preparation for removing noise from the collected light amplitude signals, calculate the root mean square (RMS) of a set of light amplitude measurements. The RMS corresponds to a value which, when multiplied by a signal-to-noise ratio (SNR), yields a noise threshold used to filter light amplitude measurements not associated with a pulse. The SNR may be any predetermined ratio that represents a ratio between signal values and noise values. For example, the SNR may be an amplitude measurement associated with a scaled value of a standard deviation from one or more light amplitude measurements.

To calculate the RMS, the controller "C" iterates across the array of light amplitude measurements stored in the memory 204 of the controller "C" and, based on the light amplitude measurements, calculates the root mean square (RMS) for one or more of the light amplitude measurements that occur at maximum pressure, before pressure begins to decrease (block 516). The RMS is calculated by squaring a particular set of light amplitude measurements stored in the memory 404 (including subsets, and forward-looking sets of light amplitude measurements), adding the squares of the light amplitude measurements, dividing the added squares by the total amount of light amplitude measurements and taking the square root of the resulting sum, the result of which is equal to the RMS of the amplitude measurements. In embodiments, the RMS may be calculated during for each amplitude measurement looking forward (e.g., the RMS may be calculated from a first point to a second point of time $t=1, 2, \ldots$ to time $t=n$, where $t=1$ represents the instant light amplitude measurement for which the RMS is being calculated). Once the RMS is calculated for one or more light amplitude measurements, the light amplitude measurements that are less than the noise threshold (e.g., less than the RMS multiplied by the SNR), are identified as noise. If all of the measured amplitudes are determined to be noise the controller "C" causes an error signal to be transmitted at block 528 indicating that no pulses were identified during operation of the tissue property sensing device 10.

If any particular light amplitude measurement is greater than the noise threshold, the light amplitude measurement is identified as associated with, or indicative of, a pulse. To determine the time at which each particular pulse begins, the controller "C" identifies, at block 522, each light amplitude measurement greater than the noise threshold. To divide the light amplitude measurements into particular pulses, when analyzing each of the light amplitude measurements successively (iterating across the array of light amplitude measurements stored in the memory 404), a first light amplitude measurement identified as being greater than the noise threshold is identified as a beginning of a pulse. The pulse continues from the time at which the first light amplitude measurement was taken until a light amplitude measurement is identified as having a measurement less than the previous light amplitude measurement (e.g., where a first light amplitude measurement has a first value, and a second light amplitude measurement temporally located after the first light amplitude measurement has a second value which is less than the first light amplitude measurement), at which time a pulse crest is identified. (see FIG. 8) In embodiments, each particular pulse is identified as occurring at the point at which the pulse crests. The pulse subsequently terminates at the time which the successive light amplitude measurements fall below the noise threshold.

In embodiments, each pulse may be associated with the initial rise of a light amplitude measurement above the lower light amplitude threshold (e.g., the beginning of a pulse) and extending continuously until a later light amplitude measurement is identified as having a value less than the lower amplitude threshold. A marker may be included at any of the mentioned pulse points, e.g., at the beginning of each pulse, the crest of each pulse, or the end of each pulse, to indicate the position of the pulse relative to all of the light amplitude measurements. The crest of the pulse may be associated with a light amplitude measurement at which the light amplitude measurements measured prior are increasing in intensity, and the light amplitude measurements measured after are decreasing in intensity (see "peak," FIG. 8).

At block 524, the controller "C" analyzes the light amplitude measurements stored in the memory 404 (see block 506) to determine the time and pressure associated with the systolic blood pressure of the patient. More particularly, the pressure associated with the first identified pulse (e.g., the first set of light amplitude measurements identified by the controller "C" once the pressure in the bladder "B" fell below the upper pressure threshold (see block 514)) is identified by the controller "C" as the pressure and time at which blood flow returned to target tissue after occlusion, commonly referred to as the systolic blood pressure. Similarly, the pressure associated with the last identified pulse (e.g., the last set of successive light amplitude measurements determined not to be noise measurements) is identified by the controller "C" as the pressure and time at which occlusion terminated, commonly referred to as the diastolic pressure. Optionally, to determine a pulse rate, at block 526 the particular pulses are counted in the array of amplitude signals which are identified as pulses and divided by the total time in which the tissue property sensing device 10 was collecting light amplitude measurements. The resulting frequency measurement is then converted to any suitable standard (e.g., pulses per minute), and a signal is transmitted by the controller "C" to display the rate at which pulses were measured. In embodiments, the controller "C" may identify a pulse as associated with the diastolic pressure of a patient as the first pulse in which none of the light amplitude measurements exceed a diastolic threshold (e.g., a threshold greater than the noise threshold, but less than the upper operational threshold of the tissue property sensing device 10).

Referring now to the amplitude transformation method (method B), once the amplitude and pressure measurements are captured (blocks 506 and 508), and the controller "C" determines that the pressure in the bladder "B" is less than the lower threshold at block 510, systolic and diastolic pressures are identified by analyzing a first and a second derivative of the collected amplitude signals.

Initially, once the pressures and amplitudes are identified and associated with particular times, process 500 may continue to block 530 and identify the point at which depressurization began. More particularly, after the bladder "B" is fully pressurized (e.g., is pressurized to a pressure above an operational threshold) the controller "C" may identify a start and stop point at which the pressure is equal to the upper and lower operational pressure thresholds, respectively. To identify the start point, the controller "C" identifies the point at which the pressures in the bladder "B" began to decrease after the pressure was reduced to match the upper operational threshold. Conversely, the stop point is identified as the last time where pressure in the bladder "B" was recorded as being greater than the lower operational threshold. For purposes of clarity, reference to the pressure and amplitude measurements will be discussed in relation to the period of time bound by the start point and the stop point.

Once the start and stop points are identified among the stored pressures and amplitudes, the controller "C" identifies a peak amplitude at block 532. To identify the peak amplitude, the second derivative of the array of amplitude measurements is calculated, referred to herein as the derived amplitude measurements. The controller "C" then iterates across the derived amplitude measurements and identifies the amplitude with the largest absolute value as being the maximum or peak measured amplitude.

Figure 8:
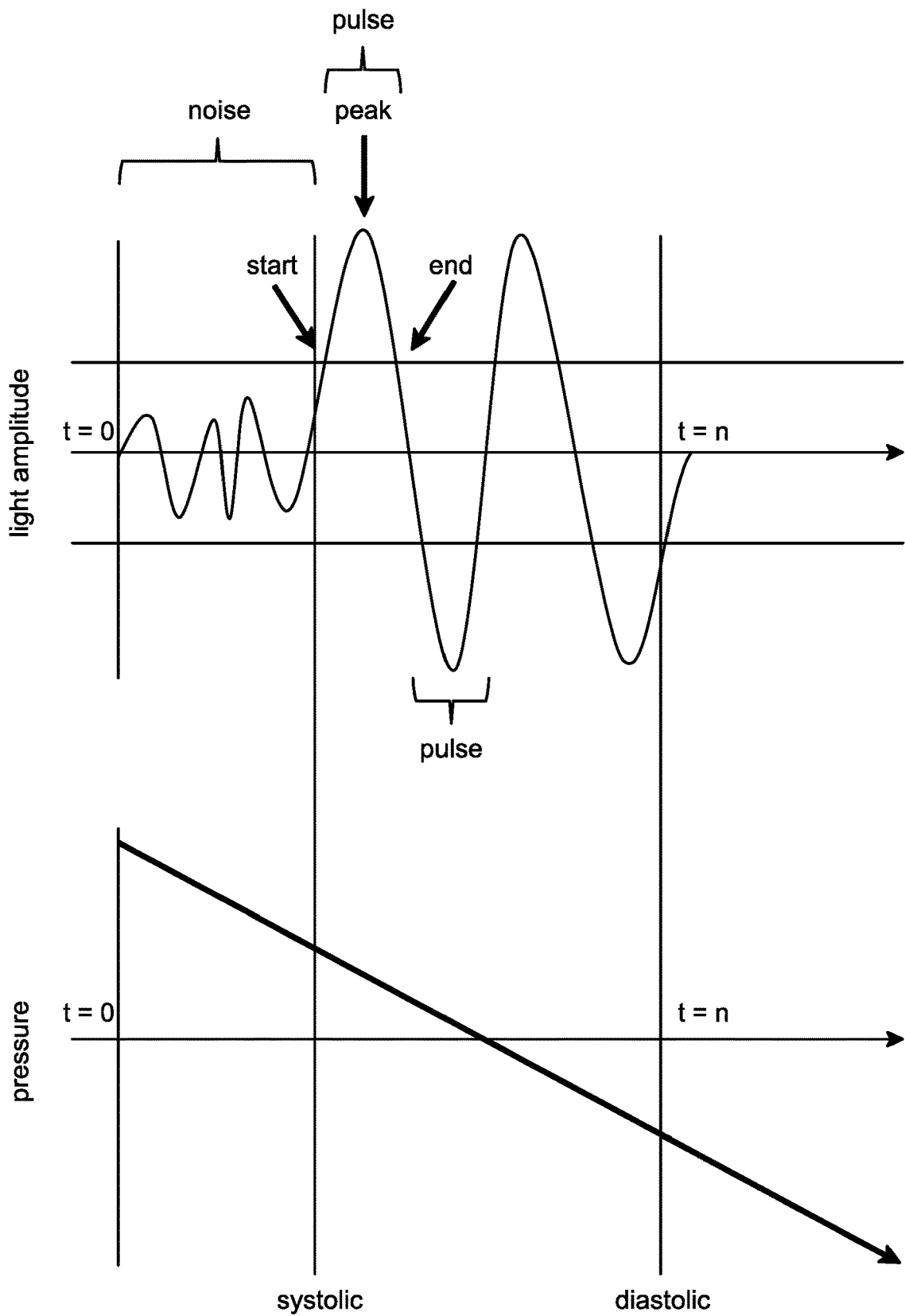
FIG. 8 illustrates sensor measurements taken during operation of the tissue property sensing device of FIG. 1.

At block 534, the controller "C" identifies the beginning of each pulse among the amplitude measurements (see FIG. 8). Initially, each amplitude measurement is set as not being associated with a pulse. As each of the derived amplitude measurements is analyzed (from time t=0 to time t=n) where the absolute value of the derived amplitude measurement is greater than a pulse threshold (e.g., the derived amplitude is greater than 25% of the peak amplitude) and the preceding derived amplitude is less than the pulse threshold, the derived amplitude measurement is identified as the beginning of a pulse. The following derived amplitude measurements taken after the derived amplitude measurement being analyzed are identified as pulse measurements until a derived amplitude measurement is identified which falls below the pulse threshold, at which point the pulse ends. This pulse period analysis is performed iteratively for all of the derived amplitude measurements.

At block 536, the controller "C" identifies the measured pressure which corresponds to the first identified pulse as the systolic pressure. Additionally, to identify the diastolic pressure, the controller "C" identifies the pressure taken during the last recorded pulse as the diastolic pressure. It should be noted that the systolic and diastolic pressures may be selected as any pressure measured during the first or last pulse, respectively (e.g., at the beginning of the pulse, at the peak or crest of the pulse, or at the end of the pulse). Alternatively, the pressures may be taken as the average of the recorded pressure measurements taken during the first or last pulse. Similar to blocks 516 and 518, at blocks 538 and 540 the controller "C" calculates the RMS of the derived amplitude measurements. If any amplitude signals are identified as being less than the RMS multiplied by the SNR, the controller "C" identifies the amplitude measurements as noise signals. If none of the derived amplitude measurements exceeds the noise signal threshold the controller "C" causes an error signal to be displayed. Alternatively, if at least one amplitude measurement exceeds the noise signal, then the controller "C" causes the systolic and diastolic blood pressures to be displayed. Optionally, at block 546 the controller "C" may determine the average pulse rate of the identified pulses similar to the determination at block 526.

Although the illustrative embodiments of the present disclosure have been described herein, it is understood that the disclosure is not limited to those precise embodiments, and that various other changes and modifications may be affected therein by one skilled in the art without departing from the scope or spirit of the present disclosure. All such changes and modifications are intended to be included within the scope of the present disclosure.

What is claimed is:

1. A method of detecting a tissue property during a laparoscopic surgical procedure with a tissue property sensing device, the method comprising:
    positioning a sensing assembly disposed along a distal portion of a tissue property sensing device about target tissue in a body cavity;
    inflating a bladder of the sensing assembly to compress and occlude blood flow of the target tissue;
    sensing a plurality of pressure measurements of pressure in the bladder and a corresponding plurality of light amplitude measurements of light projected through the target tissue taken at a plurality of times as pressure in the bladder is reduced; and
    determining a systolic blood pressure of the target tissue by:
        calculating a root mean square (RMS) of the plurality of light amplitude measurements;
        determining a noise threshold by multiplying the RMS by a signal to noise ratio (SNR);
        filtering out light amplitude measurements of the plurality of light amplitude measurements that are less than the noise threshold;
        identifying a pulse based on a light amplitude measurement of the plurality of light amplitude measurements being greater than the noise threshold; and
        determining the systolic blood pressure based on a pressure measurement of the plurality of pressure measurements associated with the pulse.

2. The method of claim 1, further comprising determining whether the pressure in the bladder is less than or equal to a lower operational threshold.

3. The method of claim 1, wherein sensing includes waiting to sense the plurality of pressure measurements and the plurality of light amplitude measurements until the pressure in the bladder is less than or equal to an upper operational threshold.

4. The method of claim 1, further comprising determining a systolic blood pressure based on the pressure measurements associated with a first pulse exceeding a predetermined threshold associated with a systolic blood pressure range.

5. The method of claim 1, further comprising determining a diastolic blood pressure based on the pressure measurements associated with a last pulse falling below a predetermined threshold associated with a diastolic blood pressure range.

6. The method of claim 1, further comprising identifying a plurality of pulses.

7. The method of claim 6, further comprising determining a pulse rate based on the identified plurality of pulses.

8. The method of claim 6, further comprising determining a systolic blood pressure based on pressure measurements of the plurality of pressure measurements associated with the plurality of pulses.

9. The method of claim 6, further comprising determining a diastolic blood pressure based on pressure measurements of the plurality of pressure measurements associated with the plurality of pulses.

10. The method of claim 1, further comprising determining a systolic blood pressure based on pressure measurements of the plurality of pressure measurements associated with a first pulse.

11. The method of claim 1, further comprising determining a diastolic blood pressure based on pressure measurements of the plurality of pressure measurements associated with a last pulse.

12. The method of claim 1, further comprising identifying a systolic blood pressure based on the sensing,
    wherein sensing includes sensing a first pressure measurement and a first light amplitude measurement taken at a first time, and a second pressure measurement and a second light amplitude measurement taken at a second time, the first light amplitude measurement being less than the second light amplitude measurement.

13. The method of claim 1, further comprising identifying a start point and a stop point of depressurization based on the plurality of pressure measurements.

14. The method of claim 1, further comprising identifying a plurality of pulses based on the plurality of light amplitude measurements.

15. The method of claim 14, further comprising identifying a systolic blood pressure based on the plurality of pulses, the systolic blood pressure being the pressure measured at a first pulse from among the plurality of pulses.

16. The method of claim 14, further comprising identifying a peak light amplitude measurement based on the plurality of light amplitude measurements.

17. The method of claim 16, further comprising identifying a beginning of each pulse, wherein the beginning of each pulse occurs at the time where a light amplitude measurement is both greater than a previous light amplitude measurement and a light amplitude threshold, the light amplitude threshold calculated as the value of the peak light amplitude measurement multiplied by a predetermined value.

18. The method of claim 17, further comprising identifying a systolic blood pressure based on pressure measurements of the plurality of pressure measurements associated with a first pulse.

19. The method of claim 18, further comprising identifying a diastolic blood pressure based on pressure measurements of the plurality of pressure measurements associated with a last pulse.

20. The method of claim 1, further comprising transmitting an error signal when no pulse is identified.

21. The method of claim 1, further comprising transmitting a signal to display the systolic blood pressure.

\* \* \* \* \*